(12) United States Patent
Yoon et al.

(10) Patent No.: US 8,252,948 B2
(45) Date of Patent: Aug. 28, 2012

(54) FAT COMPOSITION

(75) Inventors: Dong-Hun Yoon, Seoul (KR);
Moon-Won Lee, Chungcheongbuk-do (KR)

(73) Assignee: Ilshin Wells Co., Ltd., Cheongwon-gun (KR)

( * ) Notice: Subject to any disclaimer, the term of this patent is extended or adjusted under 35 U.S.C. 154(b) by 263 days.

(21) Appl. No.: 12/416,821

(22) Filed: Apr. 1, 2009

(65) Prior Publication Data

US 2009/0246299 A1    Oct. 1, 2009

Related U.S. Application Data

(63) Continuation-in-part of application No. 10/510,700, filed as application No. PCT/KR2004/000511 on Mar. 12, 2004, now abandoned.

(30) Foreign Application Priority Data

| Apr. 25, 2003 | (KR) | 10-2003-0026515 |
| Mar. 9, 2004 | (KR) | 10-2004-0015668 |
| Nov. 4, 2008 | (KR) | 10-2008-0108689 |
| Nov. 4, 2008 | (KR) | 10-2008-0108690 |

(51) Int. Cl.
| C11B 5/00 | (2006.01) |
| A61K 36/18 | (2006.01) |
| A61K 36/185 | (2006.01) |
| A61K 36/61 | (2006.01) |
| A61P 3/10 | (2006.01) |
| A61P 35/00 | (2006.01) |
| A61P 9/10 | (2006.01) |
| A61P 39/06 | (2006.01) |

(52) U.S. Cl. ............. 554/7; 424/725; 426/49; 426/542
(58) Field of Classification Search ............ None
See application file for complete search history.

(56) References Cited

U.S. PATENT DOCUMENTS

| 5,461,170 A | 10/1995 | Miyamoto et al. |
| 6,177,580 B1 | 1/2001 | Timmermann et al. |
| 6,432,453 B1 | 8/2002 | Krumhar |
| 7,090,886 B2 | 8/2006 | Koike et al. |
| 7,141,265 B2 | 11/2006 | Sakuma et al. |
| 2002/0147356 A1 | 10/2002 | Bonsignore et al. |
| 2006/0051435 A1* | 3/2006 | Udell et al. .................. 424/725 |
| 2007/0141220 A1* | 6/2007 | Lee et al. ..................... 426/601 |

FOREIGN PATENT DOCUMENTS

| DE | 197 06 951 A1 | 8/1998 |
| EP | 0 964 975 B1 | 12/1999 |
| EP | 1 174 416 A1 | 1/2002 |
| EP | 1 281 750 A3 | 2/2003 |
| EP | 1 097 708 B1 | 9/2003 |
| KR | 2004081733 A * | 9/2004 |

OTHER PUBLICATIONS

Hsu et al. Effect of gallic acid on high fat diet-induced dyslipidaemia, hepatosteatosis and oxidative stress in rats. British Journal of Nutrition (2007), 98, 727-735.*

Huang et al. Anti-diabetic action of *Punica granatum* flower extract: Activation of PPAR-γ and identification of an active component. Toxicology and Applied Pharmacology 207 (2005) 160-169.*

* cited by examiner

*Primary Examiner* — David J Blanchard
*Assistant Examiner* — Peter Anthopolos
(74) *Attorney, Agent, or Firm* — Birch, Stewart, Kolasch & Birch, LLP

(57) ABSTRACT

The present invention relates to fat composition, more specifically relates to 60% to 99.9% by weight of diglyceride containing 0.1 to 89.9% by weight of conjugated linoleic acid; 0.001% to 0.2% by weight of banaba extracts fermented by microorganism such as *Bacillus* sp. or *Aspergillus* sp.; and the balance being monoglyceride, triglyceride or a mixture thereof.

The fat composition of the present invention comprises fermented banaba extracts as an antioxidant, and the fat composition excels in oxidation stability and keeping stability, therefore the fat composition of the present invention may be widely used as cooking oil.

13 Claims, No Drawings

FAT COMPOSITION

This application is a Continuation-In-Part of U.S. application Ser. No. 10/510,700, filed Oct. 8, 2004, now abandoned, which was filed as PCT application Ser. No. PCT/KR2004/000511 on Mar. 12, 2004, which designated the United States and claims priority under 35 U.S.C. §119 to Korean Patent Application Nos. 10-2003-0026515 and 10-2004-0015668 filed on Apr. 25, 2003 and Mar. 9, 2004, respectively and on which priority is claimed under 35 U.S.C. §120. This application also claims priority under 35 U.S.C. §119 to Patent Application Nos. 10-2008-0108689 and 10-2008-0108690 filed on Nov. 4, 2008. All of the above-identified applications are hereby expressly incorporated by reference into the present application.

TECHNICAL FIELD

The present invention relates to fat composition, more specifically relates to 60% to 99.9% by weight of diglyceride containing 0.1 to 89.9% by weight of conjugated linoleic acid; 0.001% to 0.2% by weight of banaba extracts fermented by microorganism such as *Bacillus* sp. or *Aspergillus* sp.; and the balance being monoglyceride, triglyceride or a mixture thereof.

BACKGROUND ART

Conjugated linoleic acid (CLA) is a conjugated isomer of linoleic acid (LA), which is an essential fatty acid that is a naturally occurring fatty acid found in the breast milk or muscle of ruminants in a trace amount. CLA is a general term used to name positional and geometric isomers of linoleic acid having conjugated double bonds in cis- or trans-configuration. Among those CLA isomers, physiologically functional cis-9, trans-11 octadecadienoic acid and trans-10, cis-12 octadecadienoic acid are specifically referred to as the CLA. The CLA is excellent in reducing incidence of sclerosis of the artery (Artery, 1997, 22:266-277), enhancing immunogenicity (J. Nut., 1999, 129:32-38) and anti-cancer activity (Anticancer research, 1997, 17:969-973), promoting growth (J. Nut., 2000, 130:2981-2989) and therapeutic effects with respect to diabetes or other diseases. Further, the CLA has been reported to suppress obesity by reducing body fat (Am. J. Physiol., 1998, 275:R667-R672). By virtue of such properties, the CLA can be advantageously used as the effective component of functional food and pharmaceutical products.

In general, human ingest glyceride of CLA through foods prepared by esterification of CLA and glycerol. These examples are disclosed in U.S. Pat. No. 6,432,453 and US Pat. Publication No 2002/0147356 etc.

Glycerides synthesized by an esterification reaction are classified into monoglycerides (MG), diglycerides (1,2-DG, 1,3-DG, 2,3-DG), and triglycerides (TG) according to the degree of substitution of hydroxyl group.

Diglycerides are fat compositions in which fatty acid(s) and 1-, 2-, or 1- and 3-position glycerin(s) are bonded by an esterification reaction and are classified differently from ordinary fats called triglycerides.

Recently, it has been reported that diglyceride has substantially the same digestion and absorption mechanisms as ordinary neutral fat and does not cause adverse physiological effects when ingested, such as a rise in the neutral fat level in human serum or accumulation of body fat, because little diglyceride is resynthesized to become neutral fat. Accordingly, research into preparation methods of such diglyceride is continuously being carried out.

But as like triglyceride, the diglyceride is hydrolyzed by various facts during keeping or processing (eg. Cooking), and as the result, free fatty acid comes into being, and the free fatty acid produces offensive smell and toxic materials via oxidation, decomposition and composition. Also, rancidity such as color change, increase of free fatty acid, increase peroxidant, change of taste and odor happens by heating cooking. Therefore antioxidant in fat composition is indispensable.

These antioxidants mean material that prevent or delay change of odor, taste, color in food, medical, cosmetic and rancidity in fat composition, and there are synthetic antioxidant and natural antioxidant.

The examples of synthetic antioxidant are t-butylated hydroxytoluene (BHT), t-butylated hydroxyanisol (BHA), t-butylated hydroxyquinone(TBHQ), aminodiphenylamine, etc, and the examples of natural antioxidant are tocopherol, rosemaric acid, catechol, caffeic acid, ascorbic acid, etc.

The afore-mentioned synthetic antioxidants such as t-butylated hydroxytoluene (BHT), t-butylated hydroxyanisol (BHA) have the problem of decomposing by heat, and giving rise to tumor, so the synthetic antioxidants are unreasonable in view point of stability. Therefore the usages of synthetic antioxidants have been decreased, while natural antioxidants have been preferred recently.

Various researches in extracting antioxidant from natural plant and using the same are actively progressing (Natural antioxidant from residual sources, Food Chem, 72, 145~171, 2001), and the representative natural antioxidant extracted from natural plant are rosemary extracts, green tea extracts, etc.

Also, potato peels extract (Utilization of potato peels extract as a natural antioxidant in soy bean oil, Food Chem, 85, 215~220, 2004), olive mill wastewater (The use of polyphenolic extract, purified hydroxytyrosol and 3,4-dihydroxyphenyl acetic acid from olive mill wastewater for the stabilization of refined oils: a potential alternative to synthetic antioxidant. Food Chem, 93, 197~204, 2005), and grape seeds (Effect of heating conditions of grape seeds on the antioxidant activity of grape seed extract, Food Chem, 97, 472~479, 2006) shows relatively high antioxidant effect.

But, the above natural antioxidants extracted from natural plants are too expensive, and show lower antioxidant effect than synthetic antioxidant, and shows uneven antioxidant effect regarding different products, and have bad heat stability restricting the usage.

Therefore, research on fatty acid comprising plant-extracted antioxidant of improved stability and antioxidant effect is in need.

DISCLOSURE OF THE INVENTION

Therefore, the present invention has been made in view of the above problems, and it is an object of the present invention to provide fat composition having improved oxidation stability and keeping stability.

In an aspect of the present invention, there is provided a fat composition comprising 60% to 99.9% by weight of diglyceride containing 0.1 to 89.9% by weight of conjugated linoleic acid; 0.001% to 0.2% by weight of banaba extracts fermented by microorganism such as *Bacillus* sp. or *Aspergillus* sp.; and the balance being monoglyceride, triglyceride or a mixture thereof.

BEST MODE FOR CARRYING OUT THE INVENTION

The present invention will now be described in detail.

The present inventors conducted earnest studies based on the ideas that conjugated linoleic acid had functions of effecting anti-cancer activity, reducing human body fat, enhancing immunogenicity, and preventing and/or treating diabetes and that the fat composition of high purity diglyceride comprising the conjugated linoleic acid would be advantageously useful as cosmetic emulsifiers, pharmaceutical emulsifiers, or highly functional food additives. The present invention has been completed on the basis of the above finding.

Also, while investigating the method of overcoming the low oxidation stability and increasing keeping stability of diglyceride comprising the conjugated linoleic, the inventors of the present invention confirmed that the keeping stability of the fat composition improved due to the increase of antioxidation property through the usage of fermented banaba extracts as an antioxidant agent, and the inventors finished the present invention through the above results.

The fat composition of the present invention comprises (a) 60% to 99.9% by weight of diglyceride containing 0.1 to 89.9% by weight of conjugated linoleic acid; (b) 0.001% to 0.2% by weight of banaba extracts fermented by microorganism such as *Bacillus* sp. or *Aspergillus* sp.; and (c) the balance being monoglyceride, triglyceride or a mixture thereof.

The preferable content of the diglyceride is 60 to 99.9 weight %, and more preferable content is 70 to 85 weight % regarding the function of diglyceride not accumulating body fat and preventing obesity as well as physiology activity, digestion and absorption, fat stability. If the content of the diglyceride is under the preferable content, the physiology activity of the diglyceride decreases, while if the content of the diglyceride is over the preferable content, the overall production cost increases and therefore it is not economical.

The preferable content of 1,3-diglyceride is over 50 weight % among overall content of diglyceride in view point of physiology activity.

In the fat composition of high purity diglyceride containing conjugated linoleic acid according to the present invention, the conjugated linoleic acid is preferably contained in the diglyceride in an amount of 0.1 to 89.9%. The reason of specifically defining the preferred content of conjugated linoleic acid will now be described. When the content of conjugated linoleic acid is less than 0.1%, effects of the fat composition are negligible in view of functions of effecting anti-cancer activity, reducing human body fat, enhancing immunogenicity, and preventing and/or treating diabetes. When the content of conjugated linoleic acid is greater than 89.9%, the excess gives rise to a high cost of conjugated linoleic acid, increasing the preparation cost of high-purity diglyceride, which is not effective economically.

The diglyceride, monoglyceride and triglyceride may be stemmed from vegetable fats or animal fats. The preferable fats may be palm stearin oil, canola oil, cotton seed oil, corn oil, olive oil, palm oil, palm kernel oil, coconut oil, safflower oil, beef tallow and mixture thereof, and synthetic raw material such as glycerinetripalmitin, glycerinetristearin may be engaged in need. The above raw materials may be engaged alone or mixed type.

The fat component of diglyceride, monoglyceride and triglyceride may be produced by transesterification reaction of the above raw material and glycerol or by transesterification reaction of fatty acid derived from the raw material and glycerol.

The fat composition of the present invention comprises fermented banaba extracts as antioxidants.

The banaba plant belongs to Lythraceae called *Lagerstroemia speciosa*, and is leaf fall tree and is distributed through tropics from north Australia, Philippine, Malay Peninsula, Indonesia peninsula, south China, India, and is called as a crape-myrtle. As known from the name, the banaba belong to crape-myrtle, and the height ranges from 5 to 20 cm, and the trunk feels smooth, and the bark drops irregularly, and the leaf shapes thick oval, and the end of the leaf is sharp, and the length of the leaf reaches 25 cm. The banaba has been known as a medicinal plant from old times at Southeast Asia. The leaf of banaba is used to cure and prevent diabetes.

The merits of the fermented banaba extracts are improved antioxidation property in comparison with antioxidants derived from natural plants and improved stability in comparison with synthetic antioxidants.

The preferable content of fermented banaba extracts in fat composition is 0.001 to 0.2 weight %. If the content of fermented banaba extracts is under 0.001 weight %, the taste, odor and color of the fat composition changes due to dilute antioxidation effect and rancidity. If the content of fermented banaba extracts is over 0.2 weight %, the cost increases and the stability of the fat composition decreases.

The fermented banaba extracts are prepared by fermenting banaba by microorganism such as *Bacillus* sp. or *Aspergillus* sp., and these extracts have better antioxidant effect than banaba water extracts and banaba ethanol extracts. The increase of antioxidation property of the fermented banaba extracts is presumably due to stepping up of antioxidation property by the change of glycoside to aglycone of physiology active material such as phenol material.

The phenolic compound in plant has antioxidation property, and the function of the phenolic compound is diverse according to species, content, state of extraction, state of gycoside/aglycone. Considering these results, stepping up of antioxidation property is possible by engaging fermentation extracting method than solvent extracting method and increasing active extracts contents and changing glycoside into aglycone.

The preferable content of phenolic compound in fermented banaba extract is 90 to 120 ppm to diglyceride and more preferable content is 100 to 110 ppm to diglyceride.

The fermentation is processed by *Bacillus* sp. or *Aspergillus* sp. of separate microorganism or salable. The preferable representative *Bacillus* sp. may be *Bacillus amyloliquefaciens, Bacillus subtilis* or *Bacillus licheniformis*. The preferable representative *Aspergillus* sp. may be *Aspergillus oryzae*, or *Aspergillus niger*. The more preferable microorganism may be *Bacillus oryzae* or *Aspergillus oryzae* conventionally used in fermentation foods.

The fermented banaba extracts may be preferably prepared by inoculating the above-mentioned microorganism preculture fluid to banaba, and culturing at 20 to 40° C. during 12 to 72 hours in the incubators. To enhance fermentation effect, sterilization process of banaba may be engaged. It is preferable that the microorganism is cultured within the above culturing temperature range and culturing time to culture microorganism effectively.

The microorganism preculture fluid is prepared by aerobically culturing microorganism such as *Bacillus* sp., *Aspergillus* sp. in medium.

The preferable inoculating content of microorganism preculture fluid is 0.05 to 5 weight part to banaba 100 weight part considering optimal fermentation conditions.

The fat composition of the present invention comprises banaba extracts of good antioxidation property as an antioxidant, therefore the present invention effectively restrains rancidity, and keeps functions of fat composition during long-term keeping.

A further understanding can be obtained by reference to certain preferred examples which are provided herein for purposes of illustration only and are not intended to be limiting unless otherwise specified.

EXAMPLES (1) Preparation of Fat A

Into a 3 l round flask equipped with an stirrer were added 1200 g of monoglyceride, 40 g of conjugated linoleic acid and 5 g of lipase for mixing, stirred at a stirring speed of 150 rpm, and reacted at 60° C. at a stirring speed of 150 rpm for 10 hours under Vacuum condition at 1.0 Torr, thereby preparing a oil composition of diglyceride containing conjugated linoleic acid. The fat compositions prepared were subjected to molecular distillation using a diglyceride preparation processing system manufactured by Ilshin Emulsifier Co., Ltd., Korea until monoglyceride and triglyceride are all distillation.

(2) Preparation of Fat B

Into a 3 l flask were added 135.8 g of glycerol, 1344.5 g of conjugated linoleic acid, and 5 g of lipase for mixing, stirred at a stirring speed of 150 rpm, and reacted at 60° C. at a stirring speed of 150 rpm for 10 hours under Vacuum condition at 1.0 Torr, thereby preparing a oil composition of diglyceride containing conjugated linoleic acid. Followed molecular distillation under reduced pressure of 0.04 torr at 250° C., giving an oil composition of diglyceride.

Contents of monoglyceride (MG), triglyceride (TG), diglycerides (DG), e.g., 1,2-diglyceride (1,2-DG), 1,3-diglyceride (1,3-DG), and conjugated linoleic acid (CLA) bonded to diglyceride of fat composition A to D, were measured. The measurement results are shown in Table 1.

TABLE 1

| (Unit: % by weight) | Fat A | | Fat B | |
|---|---|---|---|---|
| MG | 0.5% | CLA | 0.5% | CLA |
| 1,2-DG | 30% | 34% | 30% | 80% |
| 1,3-DG | 54.6% | | 54.6% | |
| TG | 14.9% | | 14.9% | |

(5) Preparation of Banaba Water Extracts

Banaba extracts condensed solution 0.64 kg was prepared by refluxing and heating 150 mesh size of banaba leaf 10 kg sample of 10 liter water two times at 60° C. during 6 hours. The prepared banaba extracts are water-soluble, and therefore solubilization process was processed to add into fat composition.

Banaba water extracts were agitated and solubilized at 50° C. after adding banaba extracts 40 g into propylene glycol 60 g. And the solution was fully mixed at 10,000 rpm using Homomixer at 55° C. during 10 minutes after adding glycerinemonoolate 150 g. And the solution was solubilized by adding polyglycerine polyricinoleate 50 g and mixing during 10 minutes and passing homogenizer (APV GAULIN, USA) and cooling 25° C. of weak agitation condition.

(6) Preparation of Banaba Ethanol Extracts

Banaba extracts condensed solution 0.72 kg was prepared by refluxing and heating 150 mesh size of banaba leaf 10 kg sample of 10 liter ethanol (95%) two times at 50° C. during 6 hours.

The prepared extracts were solubilized in accordance with the same manner of the above (5).

(7) Preparation of Fermented Banaba Extracts using *Bacillus* sp.

Preculture fluid was prepared by aerobically stirring culturing *Bacillus subtillus* at 30° C. during 2 days using a nutrient medium (Nutrient broth, Difco, USA).

The *Bacillus subtillus* preculture fluid 0.5 weight part was inoculated to banaba 100 weight part and cultured during 48 hours at incubators after adding 10 liter water into 150 mesh size of banaba leaf 10 kg and adding sugar (glucose 2%, w/w) and keeping 30° C., pH 6.5.

Banaba fermented supernatant was prepared by inducing inactiveness of enzyme at 85° C. during 30 minutes and centrifuging at 10,000 rpm and removing fungus body and solid. Banaba fermented extracts 1.15 kg was prepared by refluxing and heating the fermented supernatant at 60° C. during 2 hours two times. The prepared extracts were solubilized in accordance with the same manner of the above (5).

(8) Preparation of Fermented Banaba Extracts using *Aspergillus* sp.

Preculture fluid was prepared by aerobically stirring culturing *Aspergillus oryzae* at 30° C. during 2 days using a malt extract medium (maltose 1.8 g/L, glucose 6 g/L, yeast extract 1.2 g/L, malt extract 6 g/L).

The *Aspergillus oryzae* preculture fluid 0.5 weight part was inoculated to banaba 100 weight part and cultured during 48 hours at incubators after adding 10 liter water into 150 mesh size of banaba leaf 10 kg and adding sugar (glucose 2%, w/w) and keeping 30° C., pH 4.5.

Banaba fermented supernatant was prepared by inducing inactiveness of enzyme at 85° C. during 30 minutes and centrifuging at 10,000 rpm and removing fungus body and solid. Banaba fermented extracts 1.32 kg was prepared by refluxing and heating the fermented supernatant at 60° C. during 2 hours two times. The prepared extracts were solubilized in accordance with the same manner of the above (5).

Fat composition of Examples 1 to 11 and Comparative Examples 1 to 7 as shown in Table 2 were prepared using fat A to B, solubilized banaba extracts, fermented banaba extracts prepared above.

TABLE 2

| | Fat A (g) | Fat B (g) | banaba water extracts (ppm) | banaba ethanol extracts (ppm) | banaba *Bacillus* fermented extracts (ppm) | banaba *Aspergillus* fermented extracts (ppm) | Gallic acid (ppm) | Rosemary extracts (ppm) |
|---|---|---|---|---|---|---|---|---|
| Ex. 1 | 100 | | | | 100 | | | |
| Ex. 2 | | 100 | | | 100 | | | |
| Ex. 3 | 80 | 20 | | | 100 | | | |
| Ex. 4 | 100 | | | | | 100 | | |
| Ex. 5 | | 100 | | | | 100 | | |

TABLE 2-continued

| | Fat A (g) | Fat B (g) | banaba water extracts (ppm) | banaba ethanol extracts (ppm) | banaba *Bacillus* fermented extracts (ppm) | banaba *Aspergillus* fermented extracts (ppm) | Gallic acid (ppm) | Rosemary extracts (ppm) |
|---|---|---|---|---|---|---|---|---|
| Ex. 6 | 80 | 20 | | | | 100 | | |
| Ex. 7 | 80 | 20 | | | 100 | | 50 | |
| Ex. 8 | 80 | 20 | | | | 100 | 50 | |
| Ex. 9 | 80 | 20 | | | 100 | | | 50 |
| Ex. 10 | 80 | 20 | | | | 100 | | 50 |
| Ex. 11 | 80 | 20 | | | 50 | 50 | 50 | |
| Comp. Ex. 1 | 80 | 20 | 100 | | | | | |
| Comp. Ex. 2 | 80 | 20 | | 100 | | | | |
| Comp. Ex. 3 | 80 | 20 | 100 | | | | 50 | |
| Comp. Ex. 4 | 80 | 20 | | 100 | | | | 50 |
| Comp. Ex. 5 | 80 | 20 | | | | | 100 | |
| Comp. Ex. 6 | 80 | 20 | | | | | | 100 |
| Comparative Ex. 7 | 80 | 20 | | | | | | |

Experimental Example 1

(Measuring Content of Phenolic Compound)

The contents of phenolic compound in examples 1 to 11 and comparative examples 1 to 7 were measured and shown in Table 3.

The overall contents of phenolic compound were measured through Folin-Denis method using spectrophotometer (UV-1601PC, Shimadzu, Japan) by measuring optical density of examples and standard solutions at 760 nm. The standard solutions were gallic acid (Sigma-Aldrich, USA) of 0, 0.5, 1.0, 2.0, 4.0, 8.0 mg/10 ml (of 10% methanol). And the overall contents of phenolic compound of examples and comparative examples were conversed and compared using standard lines detected.

TABLE 3

| | overall phenolic compound contents to diglyceride (ppm) |
|---|---|
| Ex. 1 | 101.2 |
| Ex. 2 | 101.2 |
| Ex. 3 | 101.2 |
| Ex. 4 | 102.3 |
| Ex. 5 | 102.3 |
| Ex. 6 | 102.3 |
| Ex. 7 | 179.3 |
| Ex. 8 | 180.6 |
| Ex. 9 | 149.4 |
| Ex. 10 | 150.5 |
| Ex. 11 | 140.5 |
| Comparative Ex. 1 | 75.0 |
| Comparative Ex. 2 | 76.6 |
| Comparative Ex. 3 | 117.9 |
| Comparative Ex. 4 | 124.8 |
| Comparative Ex. 5 | 78.1 |
| Comparative Ex. 6 | 79.5 |
| Comparative Ex. 7 | — |

Referring to the above Table 3, the polyphenolic compound contents of examples 1 to 6 are higher than the polyphenolic compound contents of comparative examples 1 to 2, from these results the good oxidation stability of the present invention is presumably attributable to polyphenol extracted from banaba. In special, the fact was confirmed that the increase of phenolic compound of fat composition comprising banaba extracts fermented by microorganism compared with the banaba extracted by water or ethanol was attributable to the fermentation by microorganism.

Experimental Example 2

(Measuring Oxidation Stability)

The oxidation stability of examples 1 to 11 and comparative examples 1 to 7 were measured and shown in Table 4.

The conductivity of the each example 30 g was measured using fat stability measuring apparatus (743, Metrohm Rancimat, Switzerland) at air velocity 20 L/h, 100° C., and the induction time was calculated and the oxidation stability was valuated, and the results was shown at Table 4.

The induction time means the lapse until rancidity happens, and the longer induction time means that the rancidity delays.

TABLE 4

| | induction time (h) |
|---|---|
| Ex. 1 | 22.2 |
| Ex. 2 | 21.8 |
| Ex. 3 | 22.3 |
| Ex. 4 | 21.9 |
| Ex. 5 | 22.0 |
| Ex. 6 | 22.2 |
| Ex. 7 | 24.3 |
| Ex. 8 | 24.6 |
| Ex. 9 | 23.3 |
| Ex. 10 | 22.9 |
| Ex. 11 | 25.2 |
| Comparative Ex. 1 | 20.0 |

TABLE 4-continued

| | induction time (h) |
|---|---|
| Comparative Ex. 2 | 20.7 |
| Comparative Ex. 3 | 21.4 |
| Comparative Ex. 4 | 21.0 |
| Comparative Ex. 5 | 20.3 |
| Comparative Ex. 6 | 20.5 |
| Comparative Ex. 7 | 18.2 |

Referring the Table 4, the antioxidation stability effect of the examples to 11 was higher than the antioxidation stability effect of the comparative examples 5 to 6 engaging antioxidant agents gallic acid, rosemary extracts. And the antioxidation stability effect of the example 9 engaging fermented *Bacillus* extracts, fermented *Aspergillus* extracts and gallic acid as antioxidant agents is 38% higher than the comparative example 1 not comprising antioxidant stability agent.

Especially, the antioxidation stability effect of fat composition comprising fermented banaba extracts improved compared with the antioxidation stability effect of fat composition comprising banaba water extracts or banaba ethanol extracts.

The polyphenolic compound of the present fat composition (examples) are approximately equal with the polyphenolic compound contents of comparative examples comprising catechin or rosemary extracts, but the oxidation stability of the present invention excels than oxidation stability of the comparative examples. The excellence in oxidation stability of the present invention is presumably attributable to various natural materials that remove active oxygen and obstruct creation of free radical besides phenolic compound. In addition, it was confirmed that the fermentation extraction process was better than hot water extraction or organic solvent extraction in extracting natural materials.

From these above results, we concluded that the fat composition of the present invention comprising fermented banaba extracts was superior to the fat composition comprising conventional antioxidants in antioxidation effect.

Experimental Example 3

(Valuation of Oxidation Stability at High Temperature)

The valuation of oxidation stability at high temperature was compared through change of acid value, change of color value and taste before and after cooking by cooking potato chips as following recipe using fat compositions of examples 3, 6, 11 and comparative examples 5, 7.

Frozen potato 50 g was fried at 180° C. during 3 minutes, and the frying was repeated 100 times regarding respective conditions.

The color value measuring of potato chip before and after frying was processed using conventional Lovibond method, and in detail the color of potato was calculated by reading filter number and adding the numbers comparing standard glass color filter.

The acid value was measured by titrating 0.1N KOH after injecting samples and injecting solvent 30 ml of ether:ethanol 1:1 and adding 1% Phenolphthalein.

A sensory test of fat taste, fried potato chip taste and smoking state by 10 experts was performed by the following valuation basis.

Valuation Basis

1) Acid value increase ratio: calculating the increase ratio of acid value after frying on the basis of acid value before frying and viewing by percentage.

2) Color value varying ratio: calculating the increase ratio of red color value after frying on the basis of overall color value (10×Red+Yellow) before frying and viewing by percentage.

3) Taste of frying oil, fried potato chip:
A: never unpleasant feeling in sour, stringent and off-flavor.
B: little unpleasant feeling in sour, stringent and off-flavor.
C: a little unpleasant feeling in sour, stringent and off-flavor.
D: unpleasant feeling in off-flavor and off-taste.

4) Smoking state:
○: little smoke at 180° C.
Δ: a little smoke at 180° C.
X: much smoke at 180° C.

TABLE 5

| item | Ex. 3 | Ex. 6 | Ex. 11 | Comp. Ex. 5 | Comp. Ex. 7 |
|---|---|---|---|---|---|
| increase ratio of acid value before and after frying (%) | 35.9 | 35.0 | 30.0 | 86.6 | 95.3 |
| Varying ratio of color value before and after frying (%) | 44.6 | 41.7 | 39.6 | 99.5 | 105.7 |
| taste of frying oil after frying 100 times | A | A | A | C | D |
| smoke state after frying 100 times | ○ | ○ | ○ | X | Δ |
| Taste of fried potato | A | A | A | B | C |

As known in the above table 5, the oxidation stability of the examples 3, 6, 11 and the off-flavor and taste was higher and better than the oxidation stability, the off-flavor and taste of the comparative examples 5, 7 after 100 times frying. Therefore we concluded that the fat composition of the present invention may be preferably used as a high temperature frying oil.

Industrial Applicability

The fat composition of the present invention may be used as normal edible oil, salad oil, frying oil, margarine, fat spread, shortening oil, ice-cream, dressing oil, mayonnaise, confectionary oil, etc.

What is claimed is:

1. A fat composition consisting of:
   60% to 99.9% by weight of diglyceride containing 0.1 to 89.9% by weight of conjugated linoleic acid;
   0.001% to 0.2% by weight of fermented banaba extract as an antioxidant, the fermented banaba extract having been obtained by fermenting banaba extract using a microorganism selected from the genus *Bacillus* sp., *Aspergillus* sp., or both; and
   monoglyceride, triglyceride or a mixture thereof.

2. The fat composition according to claim 1, wherein the microorganism is selected from the group consisting of *Bacillus amyloliquefaciens*, *Bacillus subtilis*, *Bacillus licheniformis*, *Aspergillus oryzae* and *Aspergillus niger*.

3. The fat composition according to claim 1, the fermented banaba extract is prepared by (a) culturing the microorganism in a medium to obtain a microorganism preculture fluid,
(b) mixing the microorganism preculture fluid with banaba,
(c) fermenting the mixture obtained in (b) at 20 to 40° C for 2 to 72 hours in a medium,
(d) filtrating to obtain a supernatant, and
(e) refluxing and heating the supernatant.

4. The fat composition according to claim 3, wherein in the (b) step, 0.05 to 5 parts by weight of the microorganism preculture fluid is inoculated with respect to 100 parts by weight of banaba.

5. The fat composition according to claim 1, wherein the microorganism is *Bacillus subtilis* or *Aspergillus oryzae*.

6. The fat composition according to claim 3, wherein the banaba in step (b) is banaba leaf.

7. A fat composition consisting of:
   60% to 99.9% by weight of diglyceride containing 0.1 to 89.9% by weight of conjugated linoleic acid;
   0.001% to 0.2% by weight of fermented banaba extract as an antioxidant, the fermented banaba extract having been obtained by fermenting banaba extract using a microorganism selected from the genus *Bacillus* sp., *Aspergillus* sp., or both;
   monoglyceride, triglyceride or a mixture thereof; and
   additional antioxidant selected from gallic acid, rosemary extract or both.

8. The fat composition according to claim 7, wherein the microorganism is selected from the group consisting of *Bacillus amyloliquefaciens, Bacillus subtilis, Bacillus licheniformis, Aspergillus oryzae* and *Aspergillus niger*.

9. The fat composition according to claim 7, the fermented banaba extract is prepared by
   (a) culturing the microorganism in a medium to obtain a microorganism preculture fluid;
   (b) mixing the microorganism preculture fluid with banaba;
   (c) fermenting the mixture obtained in (b) at 20 to 40° C for 2 to 72 hours in a medium;
   (d) filtrating to obtain a supernatant; and
   (e) refluxing and heating the supernatant.

10. The fat composition according to claim 9, wherein in the (b) step, 0.05 to 5parts by weight of the microorganism preculture fluid is inoculated with respect to 100 parts by weight of banaba.

11. The fat composition according to claim 7, wherein the microorganism is *Bacillus subtilis* or *Aspergillus oryzae*.

12. The fat composition according to claim 7, wherein the banaba in step (b) is banaba leaf.

13. A fat composition consisting essentially of:
   60% to 99.9% by weight of diglyceride containing 0.1 to 89.9% by weight of conjugated linoleic acid;
   0.001% to 0.2% by weight of fermented banaba extract as an antioxidant, the fermented banaba extract having been obtained by fermenting banaba extract using a microorganism selected from the genus *Bacillus* sp., *Aspergillus* sp., or both;
   monoglyceride, triglyceride or a mixture thereof; and
   additional antioxidant selected from gallic acid, rosemary extract or both.

\* \* \* \* \*